United States Patent

Benett et al.

Patent Number: 5,609,608
Date of Patent: Mar. 11, 1997

[54] MINIATURE PLASTIC GRIPPER AND FABRICATION METHOD

[75] Inventors: William J. Benett, Livermore; Peter A. Krulevitch, Los Altos; Abraham P. Lee, Walnut Creek; Milton A. Northrup, Berkeley; James A. Folta, Livermore, all of Calif.

[73] Assignee: Regents of the University of California, Oakland, Calif.

[21] Appl. No.: 549,497

[22] Filed: Oct. 27, 1995

[51] Int. Cl.⁶ .................................................. A61B 17/28
[52] U.S. Cl. ......................... 606/205; 606/209; 606/211; 606/207
[58] Field of Search ........................... 606/205, 206, 606/207, 208, 209, 210, 211, 133

[56] References Cited

U.S. PATENT DOCUMENTS 5,306,287  4/1994  Becker .................... 606/205
5,454,826  10/1995  Ueda .................... 606/151

*Primary Examiner*—Michael Powell Buiz
*Assistant Examiner*—Mark S. Leonardo
*Attorney, Agent, or Firm*—L. E. Carnahan; Henry P. Sartorio

[57] ABSTRACT

A miniature plastic gripper actuated by inflation of a miniature balloon and method of fabricating same. The gripper is constructed of either heat-shrinkable or heat-expandable plastic tubing and is formed around a mandrel, then cut to form gripper prongs or jaws and the mandrel removed. The gripper is connected at one end with a catheter or tube having an actuating balloon at its tip, whereby the gripper is opened or closed by inflation or deflation of the balloon. The gripper is designed to removably retain a member to which is connected a quantity or medicine, plugs, or micro-components. The miniature plastic gripper is inexpensive to fabricate and can be used for various applications, such as gripping, sorting, or placing of micron-scale particles for analysis.

19 Claims, 4 Drawing Sheets

MINIATURE PLASTIC GRIPPER AND FABRICATION METHOD

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to micromechanism, particularly to microgrippers for use in catheter-based interventional therapies or remote micro-assembly applications, and more particularly to miniature plastic grippers and fabrication method thereof.

Microactuators for remote and precise manipulation of small objects is great interest in a wide variety of applications. The design and development effort of such microgripper devices would be useful in the art as such would apply to general microfabrication techniques and establish the infrastructure for microengineering efforts including robotics, microtechnology, precision engineering, defense, energy, and biomedical research, as well as use in medical applications, such as for catheter-based interventional therapies and remote assembly or use of micromechanical systems.

When a portion of a blood vessel weakens, it bulges and forms a aneurysm, which is one of the main reasons for strokes as the vessel finally collapses and opens. These aneurysms have traditionally been treated by surgery, where the surgeon will have to open up the area of repair before attempting to surgically repair the aneurysm by clipping it. However, many aneurysms are at critical locations such as in the brain and are either difficult and risky to operate on or it is simply impossible. For the last 20 years, pioneering doctors have used interventional neuroradiology techniques to aid the treatment of brain aneurysms. Long (1–2 meters) and narrow (i.e. 250 µm to 500 µm) catheters are pushed through the arteries in the groin up to the brain to reach the aneurysm. Existing catheter-based interventional instruments rely on simplistic and usually singular means of actuation. These techniques, including balloon angioplasty, are well-established for large vessel treatments such as in the heart. It is crucial that in order to extend this medical practice into the smaller vessels such as those in the brain, the catheter-based tools must be miniaturized. In the most recent method, platinum coils were selected to fill up the aneurysms due to their ability to fill up irregular shapes and their resistance to electrolysis in the vessels when charged. The coils are either pushed through the catheter to the aneurysm by a guide wire or released by the electrolytic dissolution of a solder joint between the guide wire of the catheter and the therapeutic device, which for neurological treatments are approximately 250 µm or less in diameter. Although the charging of the coil causes electrothrombosis around the coil, the time required to release the coil is long (4 mins. to 1 hr.) and many coils are usually needed to fill up a regular sized aneurysm. The extent to which the dissolved material affects the body is unknown and electrolysis requires long terms of current in the brain and sometimes is simply unreliable. These difficulties present potential life-threatening problems to the patient for the surgeon and clinician.

Thus, there has been a need for a micromechanism which can fit into a 250 µm diameter area and which would enable the physician to release and retrieve the coils or other therapeutic device if released at the wrong time or location. A recent approach to satisfying this need involves microgrippers fabricated using known silicon-based techniques or precision micromachining, or a combination of these techniques, with the microgrippers being actuated, for example, by shape-memory alloy (SMA) films or wires deposited on or connected to the jaws of the microgrippers. Such approach is described and claimed in copending U.S. Application Ser. No. 08/446,146, filed May 22, 1995, entitled "Microfabricated Therapeutic Actuator Mechanisms", and assigned to the same assignee.

The present invention also satisfies this need by providing a simply constructed release mechanism formed from a plastic tube, actuated by a microballoon, and which can fit into blood vessels, as well as for other applications involving gripping, sorting and positioning of micron size particles, medicines, etc. While the invention has application in various areas requiring a remotely actuated microgripper, it has particular application in catheter-based interventional therapies. The plastic gripper is made of heat-shrinkable or heat-expandable plastic tubing and is formed around a removable mandrel.

SUMMARY OF THE INVENTION

It is an object of the present invention to provide a miniature plastic gripper.

A further object of the invention is to provide a method for fabricating miniature plastic grippers.

A further object of the invention is to provide a miniature gripper capable of operating in an area as small as a 250–500 µm diameter, such as in blood vessels.

Another object of the invention is to provide a simply constructed miniature plastic microgripper which is activated by inflation and/or deflation of a miniature microballoon, mounted, for example, on the tip of a catheter.

Another object of the invention is to provide a microgripper constructed of either heat-shrinkable or heat-expandable plastic tubing having a cut in one end section thereof to form gripping surfaces or jaws and which is moved by inflation or deflation of an associated microballoon.

Other objects and advantages will become apparent from the following description and accompanying drawings. Basically, the invention involves a grip/release micromechanism, or miniature plastic gripper activated by a miniature balloon and method for fabricating same. The gripper is fabricated from either heat-shrinkable or heat-expandable plastic tubing and formed around a mandrel, after which a cut is provided in one end which results in the formation of movable gripper surfaces or jaws which are adapted to retain and/or release an object, such as medicine, plugs, particles, etc. The plastic gripper is secured to an end of a catheter, for example, having a microballoon secured at the tip end thereof and which extends into the gripper and actuates the jaws or gripper surfaces by inflation or deflation of the microballoon.

The miniature plastic gripper has numerous applications, such as gripping, sorting, or placing of micron-size particles for analysis. In addition, it can be utilized in endovascular release of embolic material for the treatment of neuro-aneurysms, placement of small plugs into ovarian tubes for contraception, and handling of miniature components, such as initial confinement fusion (ICF) targets, or other very small devices.

BRIEF DESCRIPTION OF THE DRAWINGS

The accompanying drawings, which are incorporated into and form a part of the disclosure, illustrate an embodiment of the invention and its fabrication method and, together with the description, serve to explain the principles of the invention.

DETAILED DESCRIPTION OF THE INVENTION

The invention broadly involves a grip/release micromechanism or microgripper, and more specifically a miniature plastic gripper which is inexpensively fabricated by a simple method involving a plastic tube, a mandrel for forming the gripper, and a microballoon secured to a tip of another tube, such as a catheter, for actuating the gripper. A principle feature of this microgripper of this invention, compared to the microgrippers of above-referenced Application Ser. No. 08/446,146, is its simplicity of construction and fabrication, and associated reduction in fabrication costs.

The gripper is formed from a heat-shrinkable or heat-expandable tubing. A mandrel, serving as a mold, is inserted into the tube. If heat-expandable tubing is used, either the mandrel is heated, or the tubing and mandrel are heated externally (e.g., with a heat gun) to cause the end of the tube to expand or open to allow insertion of the mandrel thereinto. When allowed to cool, the plastic tube will conform to the shape of the mandrel. The tube is then cut at one end, possibly with a laser, with the mandrel still inserted, to form the gripper prongs, gripper surface or jaws. Whereafter the mandrel is removed from the thus formed gripper. Finally, the gripper is attached to a catheter or tube having a microballoon on its tip end, such that the microballoon is inserted into the gripper, and a device to be gripped or released can be inserted into the gripper and related by the prongs or jaws thereof. Subsequent inflation of the balloon opens the gripper allowing release of the device held therein. If necessary, an elastic band can be placed around the outside of the gripper jaws for additional stiffness.

The microballoon utilized to activate the plastic gripper can be produced by various known techniques, or by a polymer micromold described and claimed in copending U.S. Application Ser. No. 08/533,425, filed Sep. 25, 1995, entitled "Polymer Micromold And Fabrication Process", and assigned to the same assignee.

Figure 6:
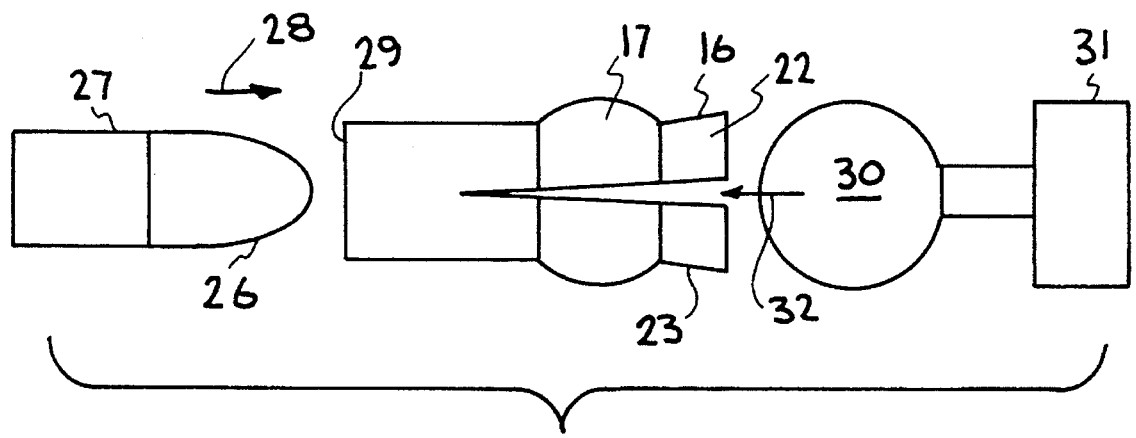
Figure 7:
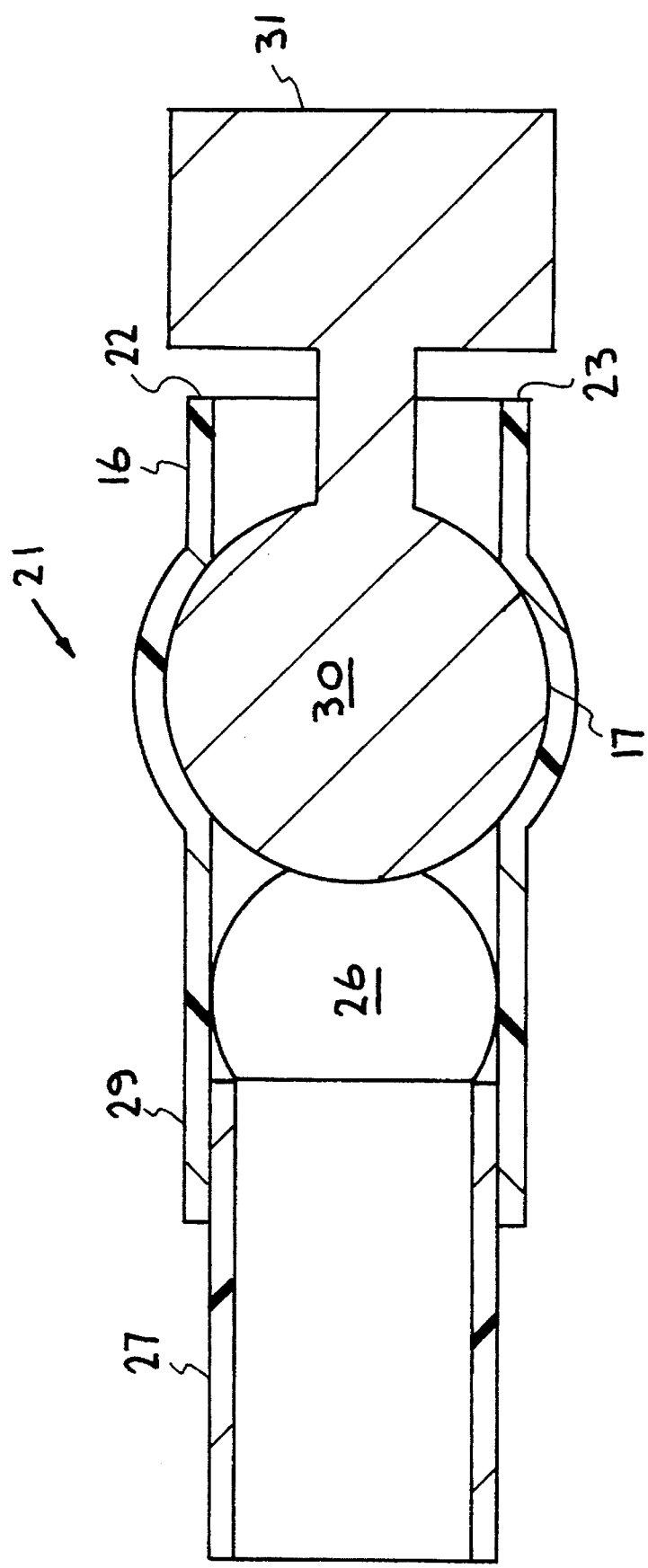
FIG. 7 is an enlarged, partial cross-sectional view of an embodiment of the invention retaining a device therein.

Referring now to the drawings, the method of fabrication of an embodiment of the miniature plastic gripper is described hereinafter with respect to FIGS. 1–6, and the thus produced gripper having a device retained therein is shown in cross-section FIG. 7. The fabrication method involves:

1. Providing a tube 10, see FIG. 1, which can be composed of either heat-shrinkable plastic or heat-expandable plastic, such as FEP Teflon, PTFE Teflon, PVC, polyolefin and neoprene having a wall thickness of 0.001 to 0.006 inch, internal diameter of 0.005 to 0.020 inch, and external diameter of 0.007 to 0.032 inch, and length of 0.040 to 0.100 inch.

Figure 1:
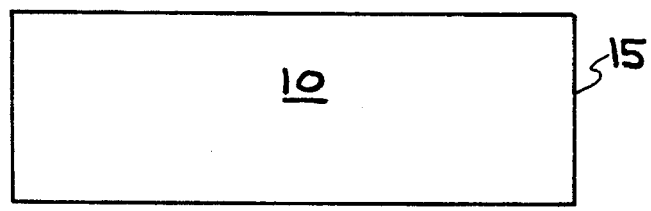
FIGS. 1–6 illustrate a fabrication method for producing an embodiment of the miniature plastic gripper in accordance with the invention.
Figure 2:
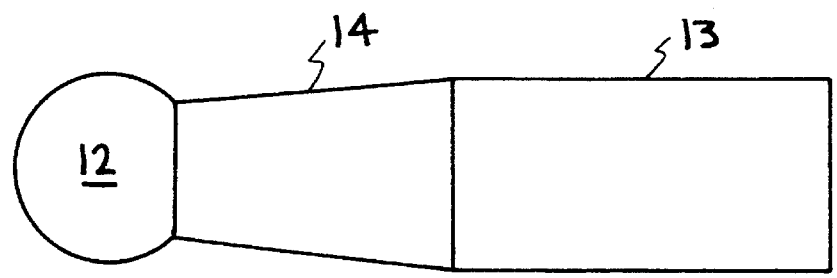

2. A mandrel, generally indicated at 11, see FIG. 2, is formed to provide a desired configuration of the plastic gripper, with the mandrel having a head section 12, and body section 13 having a tapered portion 14 adjacent head section, which can be omitted. The head section 12 of mandrel 11 may be round as shown or of other desired configuration. By way of example, the mandrel 11 may be constructed of brass, stainless steel, or aluminum, with the head section 12 having a radius of about 0.005 to 0.010 inch, the body section 13 having a diameter of 0.006 to 0.016 inch. and the tapered section 14 diameter adjacent the head section varying from 0.004 to 0.014.

Figure 3:
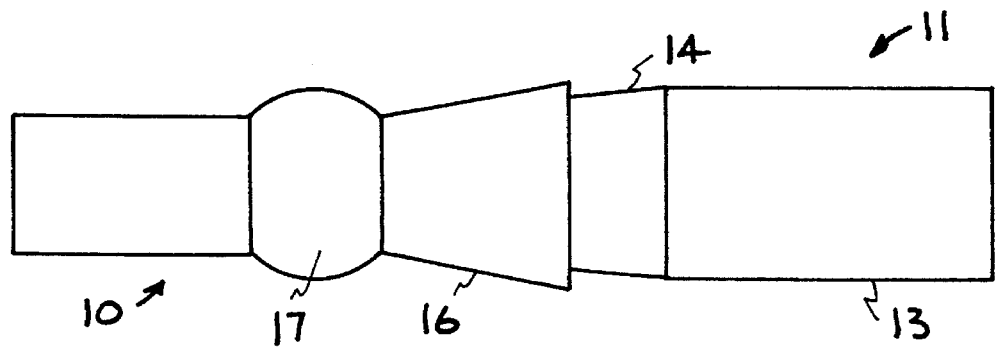

3. The mandrel 11 is inserted into one end 15 of tube 10 such that the head section 12 thereof is located at about the center of the tube and with only the tapered body section 14 extending into the tube, as shown in FIG. 3. If the tube 10 is composed of heat-shrinkable plastic, the gripper is formed by inserting the mandrel, then heating the plastic, causing it to shrink and conform to the mandrel shape.

If the tube 10 is composed of heat-expandable plastic, either the mandrel 11 is heated, or the tube 10 and mandrel are heated externally, such as by a heat gun, to cause the end section 15 of the tube 10 to open (enlarge or stretch) as indicated at 16 in FIG. 3, whereby the mandrel 11 can be inserted into the tube 10 to form an enlarged central section 17 in tube 10. By way of example, with the tube 10 composed of PTFE Teflon, the tube 10 and/or mandrel 11 are heated to a temperature sufficient to cause expansion. Note in FIG. 3 that the end section 16 of tube 10 is tapered to conform with tapered section 14 of mandrel 11.

4. The tube 10 and mandrel 11 are allowed to cool such that the plastic fully conforms to the shape of head section 12 and tapered section 14 of the mandrel.

Figure 4:
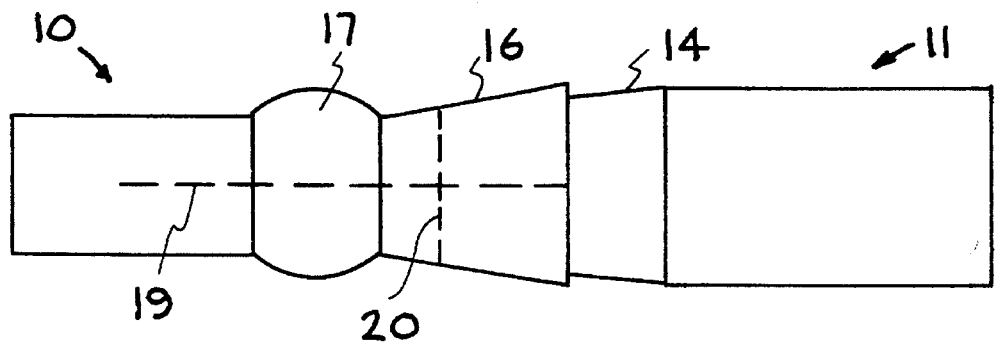
Figure 5:
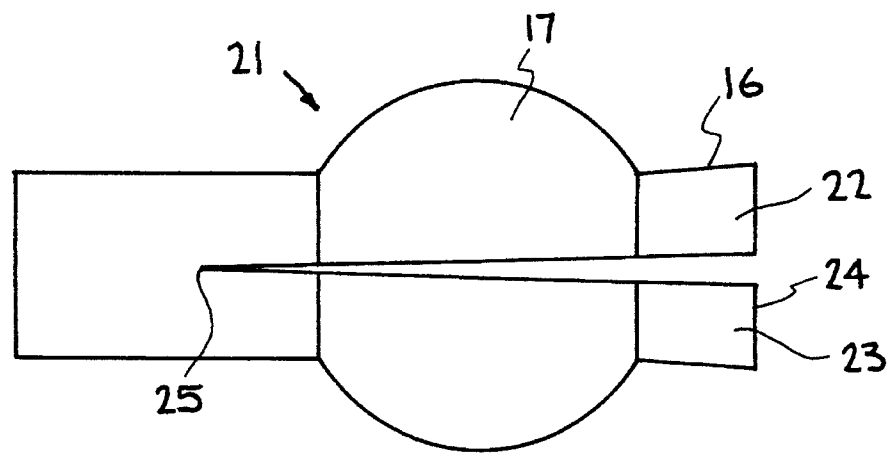

5. The tube 10 is then cut along lines 19 and 20, as seen in FIG. 4. The cuts 19 and 20 may be carried out by laser, scalpel, or a small heating tool. The cut or opening 19 enables the removal of the mandrel 11 from the tube 10 to form a gripper indicated generally at 21 in FIG. 5 having a pair of prongs or jaws 22 and 23. The location of the cut 20 determines the distance from the enlarged center section 17 to the end 24 of gripper 21 and thus the length of the tapered end section 16 thereof. The distance from center section 17 to end 24 and the taper along end section 16 determines the configuration of a device retainer to be retained in gripper 21 as described hereinafter. The cut 20 can be eliminated by positioning the head section 12 in tube 10 at an off-center location thereby moving the enlarged section 17 to the right as shown. However, merely performing the cut 20 at a desired location simplifies the fabrication process. Note that the length of the cut 19 determines the pivot point or inner end 25 of jaws 22 and 23 and thus the opening capability thereof. For example, the jaws 22 and 23 can be moved a distance of about 0.005 to 0.008 inch with respect to each other.

6. A microballoon 26 mounted on a tip of a catheter or tube 27 is inserted, as indicated by an arrow 28, into an end 29 of gripper 21 as indicated in FIG. 6, whereby inflation and deflation of balloon 26 moves jaws 22 and 23, thus completing the fabrication of the miniature plastic gripper. Also, attachment of the gripper to the catheter may be done by heat-shrinking or with a bonding agent.

As also shown in FIG. 6, a retainer 30 secured to a device 31, such as a plug, particle medicine container, etc. is inserted as indicated by arrow 32 through jaws 22–23 into enlarged section 17 of gripper 21. As the retainer 30 is inserted into gripper 21, it deforms the microballoon 26, as shown in FIG. 7. By inflation of the microballoon 26, the retainer 30 is forced from the gripper 21 and the device 31 is deposited at a desired location. The microballoon 26 may be constructed of urethane, silicone, polyurethane, latex, or any suitable elastomer.

Figure 8:
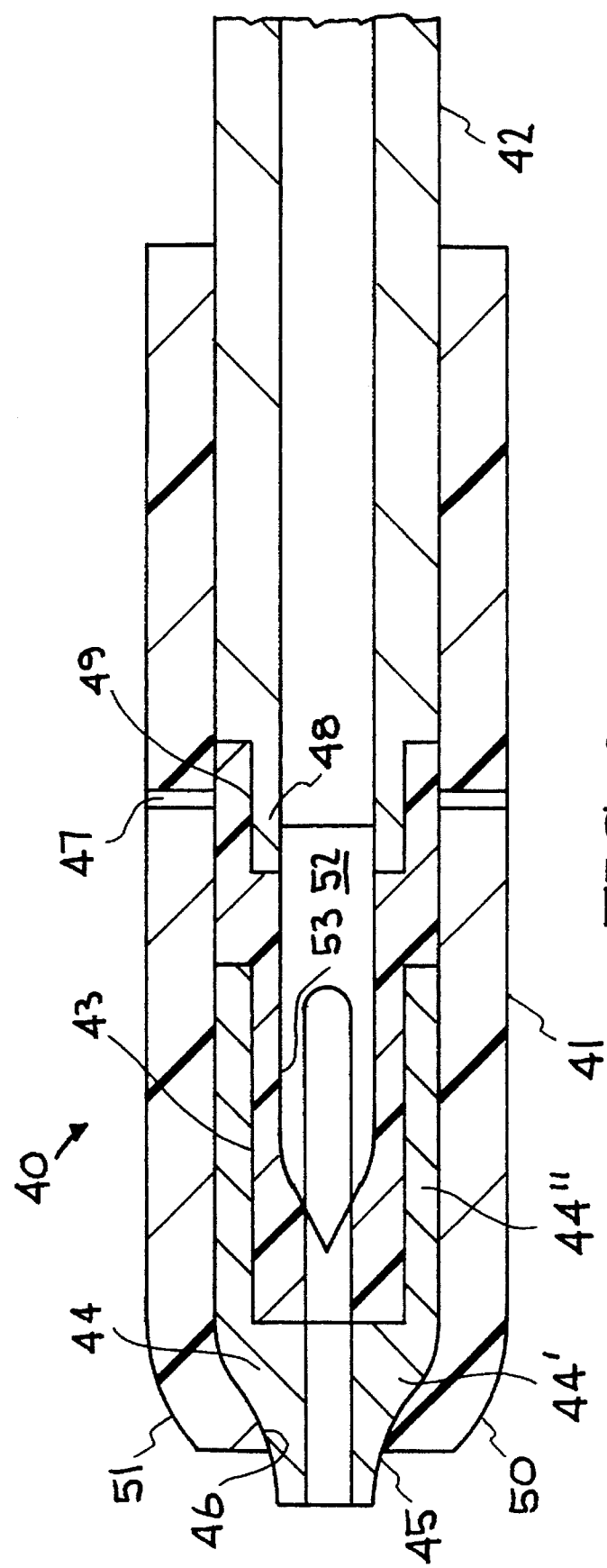
FIG. 8 is a cross-sectional view of a molded plastic release mechanism having three parts: a plastic gripper, fluid supply tube, and actuating balloon.

FIG. 8 shows in cross-section an embodiment of a molded plastic release mechanism, generally indicated at 40 which consists of three basic components: 1) a plastic gripper generally indicated at 41, 2) a fluid supply tube generally indicated at 42, and 3) an actuating balloon generally indicated at 43. As shown, a hollow mandrel 44 is located within the gripper 41 and includes a protruding section 45 which extends from an opening 46 in the end of gripper 41. During operation of the release mechanism 40, the mandrel 44 is removed and replaced with an embolic coil, for example, but could be similar to elements 30 and 31 of FIG. 7, having a spherical bead on the end adjacent the balloon 43 which preloads the balloon 43 when inserted into the gripper 41. Gripper 41 is also provided with a plurality of radially extending openings 47, two shown, which functioned as injection molding exhaust ports utilized during the formation of the balloon 43. The supply tube 42 has at the inner end a reduced diameter section 48 having a sand blasted shoulder or outer surface 49, and which extends into balloon 43. Injecting saline through the supply tube 42 inflates the balloon 43 which simultaneously pushes on the spherical bead of the coil, not shown, and opens the gripper jaws indicated at 50 and 51, thus ejecting the coil. A controlled leak is provided at the inner end of balloon 43, as described hereinafter, which allows for purging of any air trapped within the device.

The gripper 41 is manufactured, as described above, from a section of heat-shrinkable tubing which is slotted to form the opposable gripper jaws 50 and 51. After heat-shrinking the gripper 41 over the supply tube 42, using a precision-machined mandrel 44 having a head section 44' and body section 44" to form the curved gripper jaws 50 and 51, the gripper itself acts as a mold for injection-molding of the balloon 43, which may be formed of polyurethane. A sharpened glass mandrel 52 inserted through the supply tube 42 creates a cavity 53 within the balloon 43 and, once the balloon 43 is cured, the glass mandrel 52 is used to puncture the balloon end before removal from the device. The precision-machined mandrel 44 precisely controls the gap between the balloon tip and the end of the gripper by the configuration of head section 44', and also creates a gap between the balloon and the gripper wall by the body section 44", allowing for preloading of the balloon without causing any unwanted opening of the gripper jaws 50 and 51 during injection of the object to be gripped.

The following table sets forth detailed manufacturing steps for the basic components 41, 42 and 43.

| COMPONENT | MANUFACTURING STEP |
| --- | --- |
| Hydraulic Tube | Sandblast shoulder for balloon attachment. Cut tubing to length and cut slots in tubing |
| Gripper | Design and precision-machine mandrel(s) for forming gripper jaws. The mandrel is hollow for the injection-molding inlet port. Assemble gripper to hydraulic tube. Fixturing required for holding gripper, mandrel, and hydraulic tube during heat-shrinking. Drill vents in gripper for the injection-molding outlet ports (fixturing required). Sharpen glass mandrel for creating hollow balloon interior. |
| Balloon | Plunger to push excess liquid polymer through inlet port. Injection-mold the balloon, allow to cure, and |

-continued

| COMPONENT | MANUFACTURING STEP |
| --- | --- |
| | use the sharp glass mandrel to puncture the end of the balloon. |

It has thus been shown that the present invention provides a simply fabricated microgripper constructed of a plastic material utilizing a removable mandrel, and actuated by a microballoon. Thus the miniature plastic gripper can be fabricated at low cost, while being capable of delivery of a device to a desired location.

While a particular embodiment, a specific sequence of fabrication steps, and specific materials and parameters have been set forth to illustrate and exemplify the invention, such are not intended to be limiting. Modifications and changes may become apparent to those skilled in the art, and it is intended that the invention be limited only by the scope of the appended claims.

The Invention claimed is:

1. A microgripper constructed to operate in a 250–500 μm area such as a blood vessel comprising:

a body having an annular cross-section constructed of a heat deformable or moldable material;

said body including an enlarged section located intermediate two tubular configured end sections;

at least one of said tubular configured end sections being of a lesser diameter than said enlarged section;

said body including a cut extending through at least one of said tubular configured end sections and at least a portion of said enlarged section to define a pair of jaws; and means for actuating said pair of jaws adapted for retaining a device therebetween and releasing therefrom.

2. The microgripper of claim 1, wherein said cut extends partially through a second of said tubular configured end sections.

3. The microgripper of claim 1, wherein said means for actuating said pair of jaws includes a microballoon.

4. The microgripper of claim 3, wherein said microballoon is attached to an end of a tube, said end of said tube being located in a second of said tubular configured end sections of said body.

5. The microgripper of claim 1, wherein said heat deformable material is composed of a plastic.

6. The microgripper of claim 5, wherein said plastic is composed of either heat-shrinkable or heat-expandable plastic.

7. The microgripper of claim 5, wherein said plastic is selected from the group consisting of FEP Teflon, PTFE Teflon, PVC, polyolefin, and neoprene.

8. The microgripper of claim 4, wherein said microballoon is composed of material selected from the group consisting of urethane, silicone, polyurethane, latex, and other elastomers.

9. The microgripper of claim 1, wherein said one of said tubular configured end sections includes an outwardly tapered configuration.

10. The microgripper of claim 1, wherein said enlarged section of said body has an internal radius of about 0.005 to 0.010 inch and a wall thickness of 0.001 to 0.006 inch, and wherein at least said one of said tubular configured end sections has an internal tapered diameter varying from 0.004 to 0.014 inch to 0.006 to 0.016 inch, and wall thickness of 0.001 to 0,006 inch.

11. The microgripper of claim 1, wherein said pair of jaws can be moved outwardly to define a distance therebetween of 0.005 to 0.008 inch.

12. The microgripper of claim 1, wherein said body is constructed to form a mold for producing said means for actuating said pair of jaws.

13. The microgripper of claim 12, wherein said body is provided with openings which function as exit ports during formation of said jaw actuating means.

14. The microgripper of claim 3, wherein said microballoon is located intermediate an end of a fluid supply tube and said lesser diameter tubular configured end section of said body.

15. The microgripper of claim 14, wherein said microballoon is expanded by fluid directed through said supply tube.

16. The microgripper of claim 15, wherein one of said tubular configured end sections of said body is heat-shrunk onto an end of said fluid supply tube.

17. The microgripper of claim 16, additionally including means located in said fluid supply tube for puncturing said microballoon.

18. A miniature plastic gripper constructed to pass through a member of small cross-section for retaining and releasing a device comprising:

a body having a generally tubular configuration and having an enlarged section located intermediate a pair of tubular configured end sections;

said body including a cut extending through one of said pair of tubular configured end sections, through said enlarged section, and partially through a second of said pair of tubular configured end sections to define a pair of movable prongs;

a tube secured in said second of said pair of tubular configured end sections of said body; and a microballoon operatively secured to a tip of said tube and located within said body;

whereby inflation and deflation of said microballoon causes movement of said pair of movable prongs with respect to each other.

19. The gripper of claim 18, in combination with a device to be positioned by said gripper, said device including a retainer means adapted to be removably retained within said enlarged section of said body of said gripper, whereby inflation of said microballoon causes said pair of prongs of said gripper to separate whereby said retainer means can be released from said enlarged section of said body of said gripper by expansion of said microballoon.

* * * * *